United States Patent [19]

Mori et al.

[11] 4,035,087

[45] July 12, 1977

[54] CHEMICAL REACTION VELOCITY MEASURING APPARATUS

[75] Inventors: Hidetoshi Mori, Kawasaki; Teruo Shimamura, Yokosuka; Yoshio Fukami, Yokohama, all of Japan

[73] Assignee: Nippon Kogaku K.K., Tokyo, Japan

[21] Appl. No.: 641,268

[22] Filed: Dec. 16, 1975

[30] Foreign Application Priority Data

Dec. 26, 1974  Japan .............................. 50-148385
Feb. 28, 1975  Japan .............................. 50-23818

[51] Int. Cl.² ...................................... G01N 21/22
[52] U.S. Cl. ............................... 356/205; 250/565; 356/201
[58] Field of Search ........... 356/201, 205; 250/564, 250/565

[56] References Cited

U.S. PATENT DOCUMENTS 3,790,279  2/1974  Skala ................................ 250/565
3,901,600  8/1975  Johnson et al. ................... 356/205

Primary Examiner—Edward S. Bauer
Assistant Examiner—Richard A. Rosenberger
Attorney, Agent, or Firm—Fitzpatrick, Cella, Harper & Scinto

[57] ABSTRACT

An apparatus for measuring a chemical reaction velocity of a sample whose light absorbance changes in proportion to time, comprises a differential circuit for converting the absorbance signals at two different times into respective first-order differential signals, or an integrating circuit for integrating the variation of absorbance signal at two times into two integrated signals. A subtractor is provided to obtain the difference of the two differential signals or two integrated signals. The output of the subtractor is compared with a standard level by a comparing means so that abnormality signal is indicated when said difference does not fall into the standard level.

18 Claims, 14 Drawing Figures

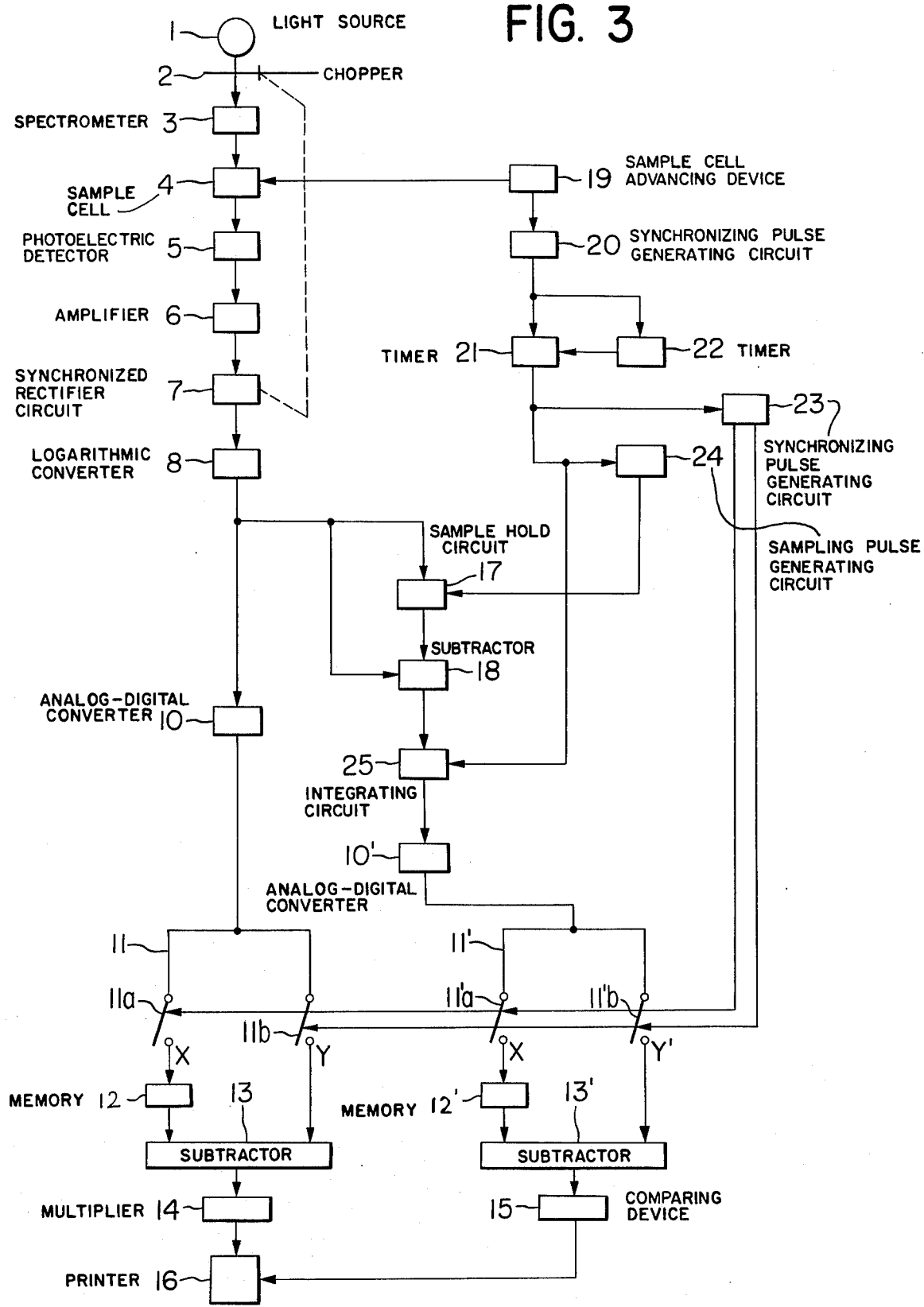

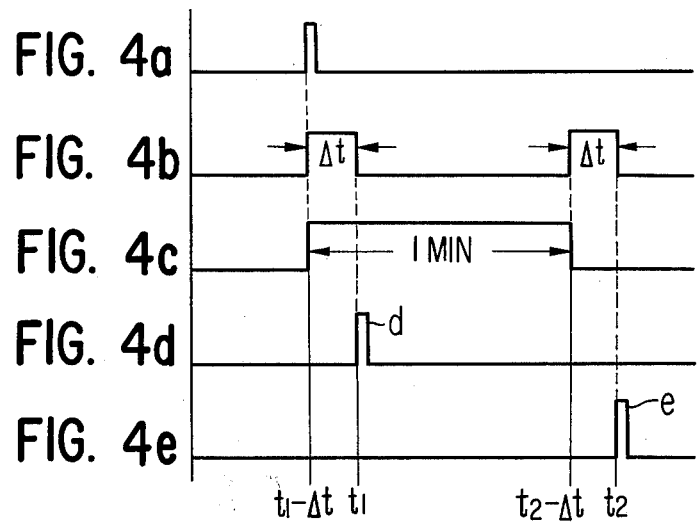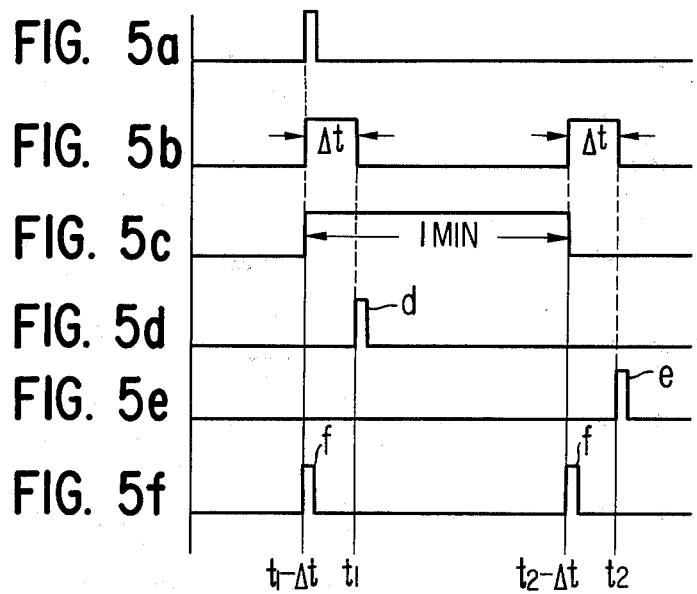

CHEMICAL REACTION VELOCITY MEASURING APPARATUS

BACKGROUND OF THE INVENTION

1. Field of the Invention

The present invention relates to an apparatus for measuring the velocity of a chemical reaction in which light absorbance changes in proportion to time.

2. Description of the Prior Art

An example of such reaction is enzymatic reaction. The determination of activity of an enzyme from a reaction thereof is usually realized by multiplying the change in absorbance in one minute (difference of absorbance/time) by a constant (hereinafter expressed as K factor) determined by the substances and conditions of measurement involved.

Also it is possible to obtain said value of the difference of absorbance/time for one minute by conversion from measurements separated by an arbitrary time interval.

In the case of enzymatic reaction, however, there usually exists a certain initial non-linear phase, called a lag phase, after the start of the reaction, and the linear reaction is reached only after such lag phase, as shown in FIG. 2 wherein the absorbance is shown as the ordinate plotted against time shown as the abscissa. For the exact determination of enzymatic activity, the measurements have to be carried out in such linear reaction portion. In the prior art the duration of such lag phase has been determined empirically and the measurements have been effected after the lapse of such duration. In such method, however, there have been no way to detect eventual error resulting from measurements being erroneously made during such non-linear period due to possible fluctuation of samples. Further such error can only be detected by checking the difference of absorbance by means of repeating plural same measurements, which inevitably lead to a drawback of longer measuring time.

The object of the present invention, therefore, is to provide an apparatus for measuring the reaction velocity which measures the absorbances $A_1$ and $A_2$ at times $t_1$ and $t_2$ to determine the difference of absorbance $\Delta A$, and simultaneously identifies and indicates whether such measurements are effected in the linear portion of the reaction.

BRIEF DESCRIPTION OF THE DRAWINGS

FIG. 3 is a diagram showing a second embodiment of the present invention;

FIGS. 4a – 4e are pulse charts explaining the function of the principal parts in the above-mentioned first embodiment;

FIG. 4a is an output signal of a synchronizing pulse generating circuit 20. FIG. 4b is an output signal of a first timer 21. FIG. 4c is an output signal of a second timer 22. FIG. 4d is an output signal from the terminal 23X of a synchronizing pulse generating circuit 23. FIG. 4e is an output signal from the terminal 23Y of a synchronizing pulse generating circuit 23.

FIGS. 5a – 5f are pulse charts explaining the function of the principal parts in the above-mentioned second embodiment; FIG. 5a is an output signal of a synchronizing pulse generating circuit 20. FIG. 5b is an output signal of a first timer 21. FIG. 5c is an output signal of a second timer 22. FIG. 5d is an output signal from the terminal 23X of a synchronizing pulse generating circuit 23. FIG. 5e is an output signal from the terminal 23Y of a synchronizing pulse generating circuit 23. FIG. 5f is an output signal of sampling pulse generating circuit 24.

DETAILED DESCRIPTION OF THE PREFERRED EMBODIMENTS

The present invention will now be explained with respect to a first embodiment thereof shown in FIG. 1 and FIG. 4 which measures the absorbances $A_1$ and $A_2$ at times $t_1$ and $t_2$ to determine the difference of absorbance $\Delta A$, simultaneously identifies whether such measurements are effected in the linear portion of a reaction by means of detecting whether the differentiated value of absorbance $(dA/dt)_{t=t_1}$ at times $t_1$ is equal to that $(dA/dt)_{t=t_2}$ at time $t_2$, and indicates the result of such identification in the output of results.

Figure 1:
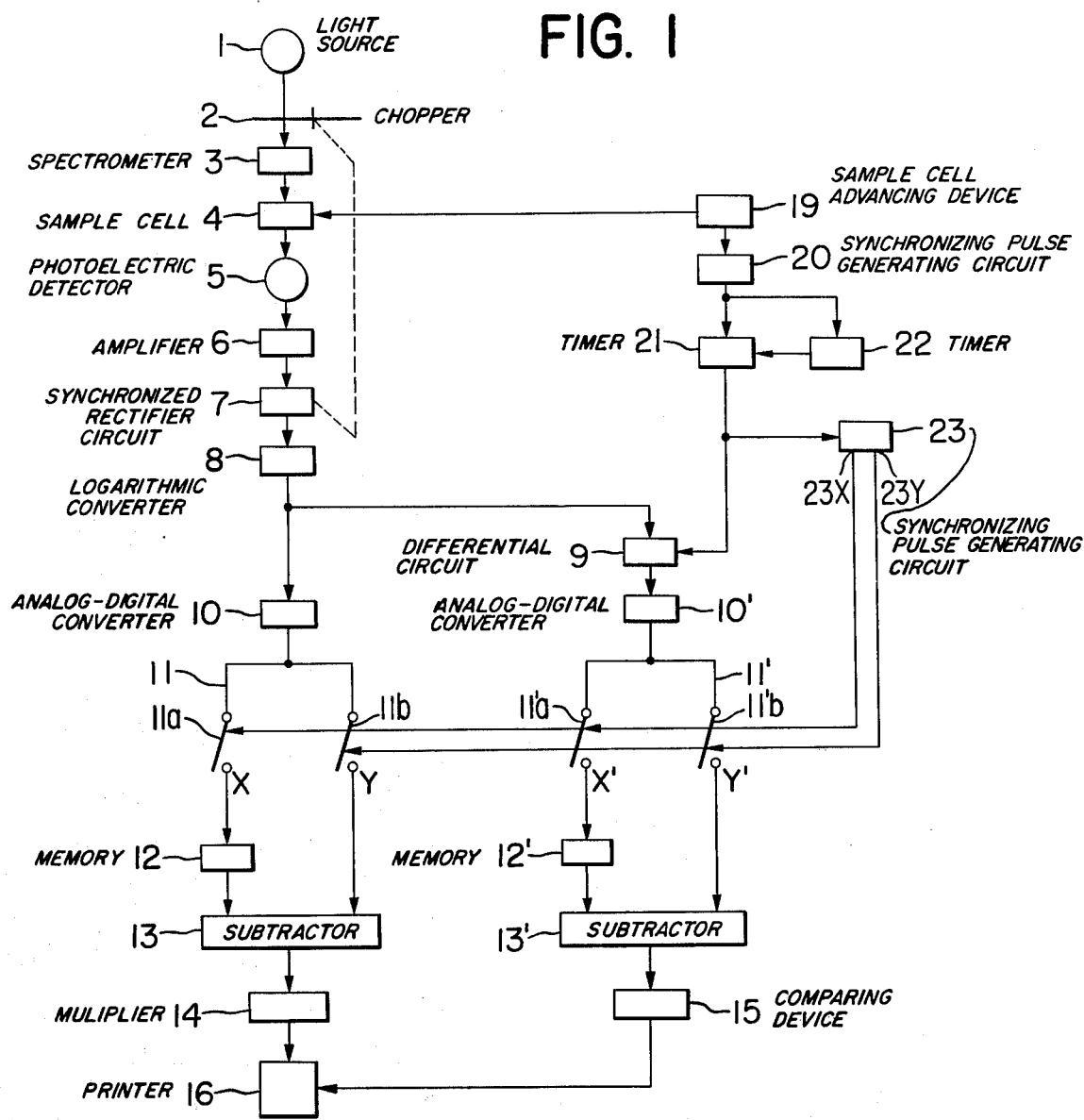
FIG. 1 is a diagram showing a first embodiment of the present invention.

Referring to FIG. 1, there are shown a light source 1, a chopper 2, a spectrometer 3 such as a monochrometer or an interference filter, a sample cell 4, a photoelectric detector 5 such as a photomultiplier, an amplifier 6 for amplifying the output signal from said photoelectric detector 5, a synchronized rectifying circuit 7 functioning in sychronization with said chopper 2, a logarithmic converter 8 of which output is on one part connected to the input terminal of a differentiating circuit 9, and on the other part connected to the input terminal of an analog-digital converter 10, and a similar analog-digital converter 10' connected to the differential circuit 9. 11 and 11' are mutually connected switches respectively provided with contacts X, Y and X' and Y', and contact arms 11a, 11b, and 11a', 11b'. Said switches are controlled by means for example of a sample advancing mechanism or a timer and are so structured that said contacts are all open in the normal state and that said contacts X and X' are closed upon receipt of a first signal from said advancing mechanism or said timer while said contacts Y and Y' are closed instead upon receipt of a succeeding signal after a determined period. 12 and 12' are memory circuits supplied with the signals from said contacts X and X' of said switches 11 and 11' to memorize the signals firstly introduced to said contacts X and X'. 13 and 13' are subtractors provided with subtrahend input terminals and minuend input terminals which are connected to the output terminals of said memory circuits 12 and 12'.

On the other hand said subtrahend input terminals are connected to the contacts Y and Y' of said switches 11 and 11'. 14 is a multiplier for multiplying the output of said subtractor 13 with a constant (aforementioned K factor), and the result of said multiplication is digitally printed by a printer 16. 15 is a comparing device such as a window comparator supplied with the output of said subtractor 13'. Said comparing device compares the output subtacted by said subtractor 13' with a predetermined tolerance level $O \pm \Delta V$, wherein $\Delta V$ is noise signal etc., and provides a signal to the printer 16 for printing when said output signal is outside the tolerance level.

19 is a sample cell advancing mechanisms for intermittently advancing the sample cell 4, and 20 is a synchronizing pulse generating circuit for generating pulse signals as shown in FIG. 4a in synchronization with the completion of each advancement of said sample cell 4. 22 is a second timer functioning for a determined period (one minute in the present embodiment) as shown in FIG. 4c upon receipt of the signal from said pulse generating circuit 20. Further, 21 is a first timer structured to function, as shown in FIG. 4b, for a period $\Delta t$ by a signal from said pulse generating circuit 20 and again for a period $\Delta t$ by an output pulse from the second timer 22 upon completion of the function thereof. Aforementioned differentiating circuit 9 is controlled by the output signal of the first timer 21 to function for a period $\Delta t$ to differentiate the signal from the logarithmic converter 8, 23 is a synchronizing pulse generating circuit which generates, in synchronization with the termination of pulse signal from the first timer 21, the pulse signals $d$ and $e$ as shown in FIG. 4d and FIG. 4e respectively from the output terminals 23X and 23Y thereof. The switch 11 is so structured that the contact arm 11a thereof comes into contact with said terminal X only upon receipt of said pulse $d$ and the contact arm 11b thereof comes into contact with said terminal Y only upon receipt of said pulse $e$, and the switch 11' is so structured that the contact arm 11'a thereof comes into contact with said terminal X' only upon receipt of said pulse $d$ and the contact arm 11'b thereof comes into contact with said terminal Y' only upon receipt of said pulse $e$.

In the present embodiment of the composition thus far explained, the light from the light source 1 is converted into an alternating signal by means of the chopper 2, and a wavelength suitable for the sample is selected by the spectrometer 3. The monochromatic light from the spectrometer 3 is subjected to absorption in the sample contained in the sample cell 4, and the transmitted light is converted by the photoelectric detector 5 to an electric signal which is subsequently amplified by the amplifier 6. Further a signal component synchronized with the chopper 2 is taken out by the synchronized rectifying circuit 7 and converted to an absorbance signal by means of the logarithmic converter 8. The absorbance signal thus obtained is converted into a digital signal by the analog-digital converter 10.

Further, as the synchronizing pulse generating circuit 20 generates the pulse shown in FIG. 4a at the completion of the advancement of the sample cell 4 by the advancing mechanism 19, the differentiating circuit 9 is activated by the pulse from the first timer 21 for a period $\Delta t$ during which the differentiating circuit 9 differentiates the absorbance signal from said logarithmic converter 8. The output signal from the differentiating circuit 9 is converted into a digital signal by means of the analog-digital converter 10'. The contact arms 11a and 11'a respectively of the switches 11 and 11' are brought into contact with the contacts X and X' upon receipt of the pulse $d$ generated by the pulse generating circuit 23 after the lapse of said period $\Delta t$ to supply the signals from the analog-digital converters 10 and 10' to the memory circuits 12 and 12' which respectively memorize the absorbance signal and the differentiated absorbance signal at the time $t_1$. The differentiating circuit 9 is again activated for a period $\Delta t$ by the signal from the first timer 21 one minute after the start of the second timer 22, and after the lapse of said period $\Delta t$ the contact arms 11b and 11'b of the switches 11 and 11' are switched to the contacts Y and Y' by the pulse from the pulse generating circuit 23 thereby supplying the absorbance signal and the differentiated absorbance signal the time $t_2$ respectively to the subtrahend input terminals of the subtractors 13 and 13' through switches 11 and 11'.

In this manner the subtractor 13 provides the difference of absorbance between $t_1$ and $t_2$, which is multiplied with the K factor by the multiplier 14 to obtain the amount of enzyme in international units, which is printed by the printer 16. Also the subtractor 13' provides the difference of differentiated absorbance between $t_1$ and $t_2$, which is compared with a predetermined tolerance range by the comparing device 15 which provides an abnormality signal only when said difference signal is located outside said tolerance range. Such abnormality signal which is printed by the printer 16 allows the user to identify that the sample has been subjected to measurements during a period in which the absorbance is not proportional to the time and thus has to be remeasured.

Figure 2:
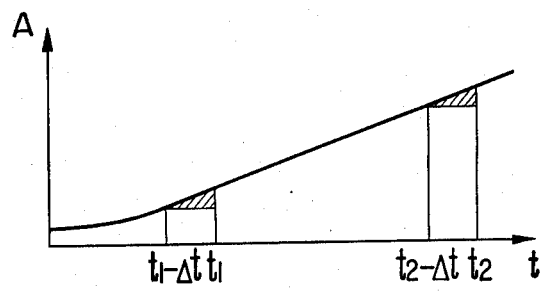
FIG. 2 is a chart showing the relation between the absorbance of the sample and reaction time.

In the following there is given a detailed explanation on a second embodiment of the present invention shown in FIGS. 3 and 5, relating to an apparatus for measuring the reaction velocity which measures absorbances $A_1$ and $A_2$ at time $t_1$ and $t_2$ to determine the difference $\Delta A$ thereof, further identifies whether such measurements are effected in the linear portion of reaction by detecting whether the integrated changes of absorbance (hatched areas in FIG. 2);

$$\int_{t_1 - \Delta t}^{t_1} \Delta A_1 dt \quad \text{and} \quad \int_{t_2 - \Delta t}^{t_2} \Delta A_2 dt$$

are mutually equal and indicates the result of such identification.

Referring to FIG. 3, 24 is a sampling pulse generating circuit which generates, upon receipt of the pulse signal shown in FIG. 5b from the first timer 21, the pulse signal as shown in FIG. 5f at the start (time $t_1 - \Delta t$ or $t_2 - \Delta t$) of each pulse from the first timer 21 to activate a sample hold circuit to be explained later. 17 is a sample hold circuit which is activated upon receipt of the pulse $f$ from the sampling pulse generating circuit 24 to hold the absorbance signal from the logarithmic converting circuit 8 at this moment for a determined period which is at least equal to said period $\Delta t$ and continues to output said signal during said period. 18 is a subtractor which receives the absorbance signal from the sample hold circuit 17 as the subtrahend input and the absorbance signal from said logarithmic converter 8 as the minuend input to provide the difference thereof. 25 is an integrating circuit which is activated upon receipt of output pulse shown in FIG. 5b from the first timer 21 for a period $\Delta t$ to integrate the absorbance signal from the subtractor 18.

In the present embodiment of the composition thus far explained, the subtractor 13 generates, in the similar manner as in the foregoing first embodiment, a signal of difference of absorbances between $t_1$ and $t_2$, which is converted by multiplication of K factor by the multiplier 14 to the amount of enzyme in international units which is printed by the printer 16. On the other hand the sample hold circuit 17 is activated upon receipt of the pulse $f$ shown in FIG. 5f generated by the sampling pulse generating circuit 24 at time $t_1 - \Delta t$ to hold the absorbance signal from the logarithmic converter 8 at this moment and to continue to output said signal for a determined period.

The subtractor 18 subtracts the absorbance signal thus maintained by the sample hold circuit 17 from the varying absorbance signal obtained from the logarithmic converter 8 starting from the time $t_1 - \Delta t$ and supplied the result of such subtraction to the integrating circuit 25, which, being activated upon receipt of pulse shown in FIG. 5b from the first timer 21 at the time $t_1 - \Delta t$, integrates the signal from the subtractor 18 for a period $\Delta t$. The output signal of the integrating circuit 25 is converted by the analog-digital converter 10' to a digital signal which is memorized, as explained before, in the memory circuit 12' through the switch 11' of which contact arm 11'a is in contact with the terminal X'. Also at $t_2$, the signal similarly integrated by the integrating circuit 25 from time $t_2 - \Delta t$ to $t_2$ is supplied to the minuend input terminal of the subtractor 13' through the switch 11' of which contact arm 11b' is in contact with the terminal Y'. The difference signal obtained from the subtractor 13' as the difference between aforementioned two integrated signals is compared with a predetermined tolerance range by the comparing device 15, which supplies an abnormality signal to the printer 16 only when said difference signal is located outside said tolerance range. Said abnormality signal printed by the printer 16 allows the user to identify that the measurements of reaction velocity have been effected in a range where the absorbance is not proportional to time and the measurements for the sample in question have to be repeated.

We claim:

1. An apparatus for measuring reaction velocity of a sample from the difference of light absorbance measurements at two different times effected during a period wherein said absorbance is proportional to the reaction time, comprising
   a differentiating circuit for converting the absorbance signals at said two times into respective first-order differential signals,
   a subtractor for obtaining the difference of said two differential signals, and
   a comparing means for comparing the output of said subtractor with a standard level,
   an abnormality signal being indicated when said difference of first-order differential signals does not fall into said standard level.

2. An apparatus for measuring reaction velocity of a sample from the difference of light absorbance of measurements at two different times effected during a period wherein said absorbance is proportional to the reaction time, comprising
   an integrating circuit for integrating the variation of absorbance signal at said two times,
   a subtractor for obtaining the difference of said two integrated signals, and
   a comparing means for comparing the output of said subtractor with a standard level,
   an abnormality signal being indicated when said difference of integrated signals does not fall into said standard level.

3. In combination with apparatus for measuring the reaction velocity of a sample from the difference of light absorbance measurements taken at two different times, means operative to identify a non-linear condition of said reaction velocity at said times, said means comprising:
   a circuit operative in response to said light absorbance measurements taken at said two times to produce control signals corresponding to the rates of change of light absorbance of said reaction velocity at each of said two different times,
   a subtractor for obtaining the difference of said two control signals, and
   means operative to produce an abnormality signal in response to the output of said subtractor when such output exceeds a predetermined standard level.

4. The combination according to claim 3, wherein said circuit to produce control signals is a differentiating circuit.

5. The combination according to claim 3, wherein said circuit to produce control signals is an integrating circuit.

6. In apparatus for measuring reaction velocity of measurements at two different times effected during a period wherein said absorbance is proportional to the reaction time, including:
   means for measuring the rate of light absorbance of the sample at two different times and indicating a value based upon the difference between said absorbance rates, the combination of
   a differentiating circuit for converting the absorbance signals at said two different times into respective first-order differential signals,
   a subtractor for obtaining the difference between said two differential signals, and
   means for comparing the output of said subtractor with a standard level.

7. The combination according to claim 6, including display means for indicating the value based upon the difference between said absorbance rates, and means for indicating the relationship of the difference between said differential signals and said standard level.

8. The combination according to claim 6, wherein said first mentioned means include means for directing light signals of a selected wavelength to a sample, means converting light transmitted from the sample to absorbance signals, and converter means converting said signal into a digital indication.

9. The combination according to claim 6, including timing means for actuating said differential circuit at said two different times.

10. The combination according to claim 7, wherein said display means is a printer.

11. The combination according to claim 8, wherein said first mentioned means include a logarithmic converter and means feeding the signals from same to said converter means and said differential circuit.

12. In apparatus for measuring reaction velocity of a sample from the difference of light absorbance measurements at two different times effected during a period wherein said absorbance is proportional to the reaction time, including:
   means for measuring the rate of light absorbance of the sample at two different times and indicating a value based upon the difference between said absorbance rates, the combination of
   an integrating circuit for integrating the variation of absorbance signals at said two times,
   a subtractor for obtaining the difference between said two integrated signals, and
   means for comparing the output of said subtractor with a standard level.

13. The combination according to claim 12, including display means for indicating the value based upon the difference between said absorbance rates, and means indicating the relationship of the difference between said integrated signals and said standard level.

14. The combination according to claim 12, wherein said first mentioned means include means for directing light signals of a selected wavelength to a sample, means converting light transmitted from the sample to absorbance signals, and converter means converting said signal into a digital indication.

15. The combination according to claim 12, including timing means for actuating said integrating circuit at said two different times.

16. The combination according to claim 13, wherein said display means is a printer.

17. The combination according to claim 14, wherein said first mentioned means include a logarithmic converter and means feeding the signals from same to said converter means and said integrating circuit.

18. A method for measuring the reaction velocity of a sample from the difference of light absorbance measurements taken at two different times, and identifying a non-linear condition of the reaction velocity at said times, comprising:
producing control signals corresponding to the rates of change of light absorbance of the reaction velocity of said sample at each of said two different times,
obtaining the difference of said two control signals, and
producing an abnormality signal in response to said difference when such output exceeds a predetermined standard level.

* * * * *